US005320641A

United States Patent [19]

Riddle et al.

[11] Patent Number: 5,320,641

[45] Date of Patent: Jun. 14, 1994

[54] COMPUTER CONTROLLED PHYSICAL THERAPY DEVICE

[75] Inventors: Ernie Riddle, Anderson County; Ron J. Withrow, McMinn County, both of Tenn.

[73] Assignee: Riddle & Withrow, Inc., Oak Ridge, Tenn.

[21] Appl. No.: 9,788

[22] Filed: Jan. 27, 1993

Related U.S. Application Data

[63] Continuation-in-part of Ser. No. 843,805, Feb. 28, 1992, and a continuation-in-part of Ser. No. 902,084, Jun. 22, 1992, Pat. No. 5,258,019.

[51] Int. Cl.[5] .......... A61F 5/00

[52] U.S. Cl. .......... 606/243; 5/618; 601/24

[58] Field of Search .......... 128/25 R; 606/241–245; 482/9, 901; 5/616, 617, 618, 622

[56] References Cited

U.S. PATENT DOCUMENTS

| | | | |
|---|---|---|---|
| 1,190,195 | 7/1916 | Schmidt . | |
| 1,628,369 | 5/1927 | McBurney . | |
| 1,830,071 | 11/1931 | Patton . | |
| 2,002,349 | 5/1935 | Lundeen . | |
| 2,104,745 | 1/1938 | Howell et al. . | |
| 2,152,431 | 3/1939 | Jensen . | |
| 2,179,595 | 11/1939 | McManis . | |
| 2,598,204 | 5/1952 | Allen . | |
| 2,749,911 | 6/1956 | Griffin . | |
| 2,865,367 | 12/1958 | Sorenson . | |
| 2,931,354 | 4/1960 | Sellner . | |
| 3,241,828 | 3/1966 | Adolphson et al. . | |
| 3,315,666 | 4/1967 | Sellner . | |
| 3,450,132 | 6/1969 | Ragon et al. . | |
| 3,623,480 | 11/1971 | Chisholm . | |
| 3,640,272 | 2/1972 | Hussey | 128/33 |
| 3,674,017 | 7/1972 | Stefani . | |
| 3,741,200 | 6/1973 | Morin | 606/243 |
| 4,144,880 | 3/1979 | Daniels . | |
| 4,379,450 | 4/1983 | Sjolinder | 606/243 |
| 4,419,989 | 12/1983 | Herbold . | |
| 4,445,504 | 5/1984 | Barge . | |
| 4,531,730 | 7/1985 | Chenera . | |
| 4,649,905 | 3/1987 | Barnes . | |
| 4,655,200 | 4/1987 | Knight . | |
| 4,691,694 | 9/1987 | Boyd et al. | 128/25 R |
| 4,723,537 | 2/1988 | Parker, Jr. . | |
| 4,724,828 | 2/1988 | Barnes et al. . | |
| 4,817,940 | 4/1989 | Shaw et al. | 482/9 |
| 4,827,913 | 5/1989 | Parker . | |
| 4,834,072 | 5/1989 | Goodman . | |
| 4,953,541 | 9/1990 | Parker, Jr. . | |
| 4,960,111 | 10/1990 | Steffensmeier . | |
| 5,014,688 | 5/1991 | Fast . | |
| 5,044,359 | 9/1991 | Reinert . | |
| 5,054,774 | 10/1991 | Belsito | 128/25 R |
| 5,099,828 | 3/1992 | Duke . | |
| 5,123,916 | 6/1992 | Riddle et al. . | |
| 5,171,260 | 12/1992 | McIlwain | 128/25 R |

FOREIGN PATENT DOCUMENTS

| | | | |
|---|---|---|---|
| 0289938 | 11/1988 | European Pat. Off. | 482/9 |

*Primary Examiner*—Richard J. Apley
*Assistant Examiner*—Jeanne M. Mollo
*Attorney, Agent, or Firm*—Pitts & Brittian

[57] ABSTRACT

A spinal diagnostics/therapy device that is computer controlled such that all motions thereof can be automated if desired. Individual and joint motions of body support portions are generated by computer controlled actuators which derive operating signals from a CPU. Memory units within the CPU and/or inserted for a particular patient control the program of the diagnostics or therapy of a patient. As a result, no physical adjustment of support elements need to be made by a person supervising the diagnostic or therapy session. During an initial session, a patient can help by inputting information as to the limits of motion that can be tolerated. For repeat sessions, the machine can be pre-programmed to give specific exercises to the spine of the patient. The actuators are provided with position sensors to produce feedback signals related to axial movement to the CPU. The actuator units are selected from electrical, pneumatic and hydraulic devices.

10 Claims, 9 Drawing Sheets

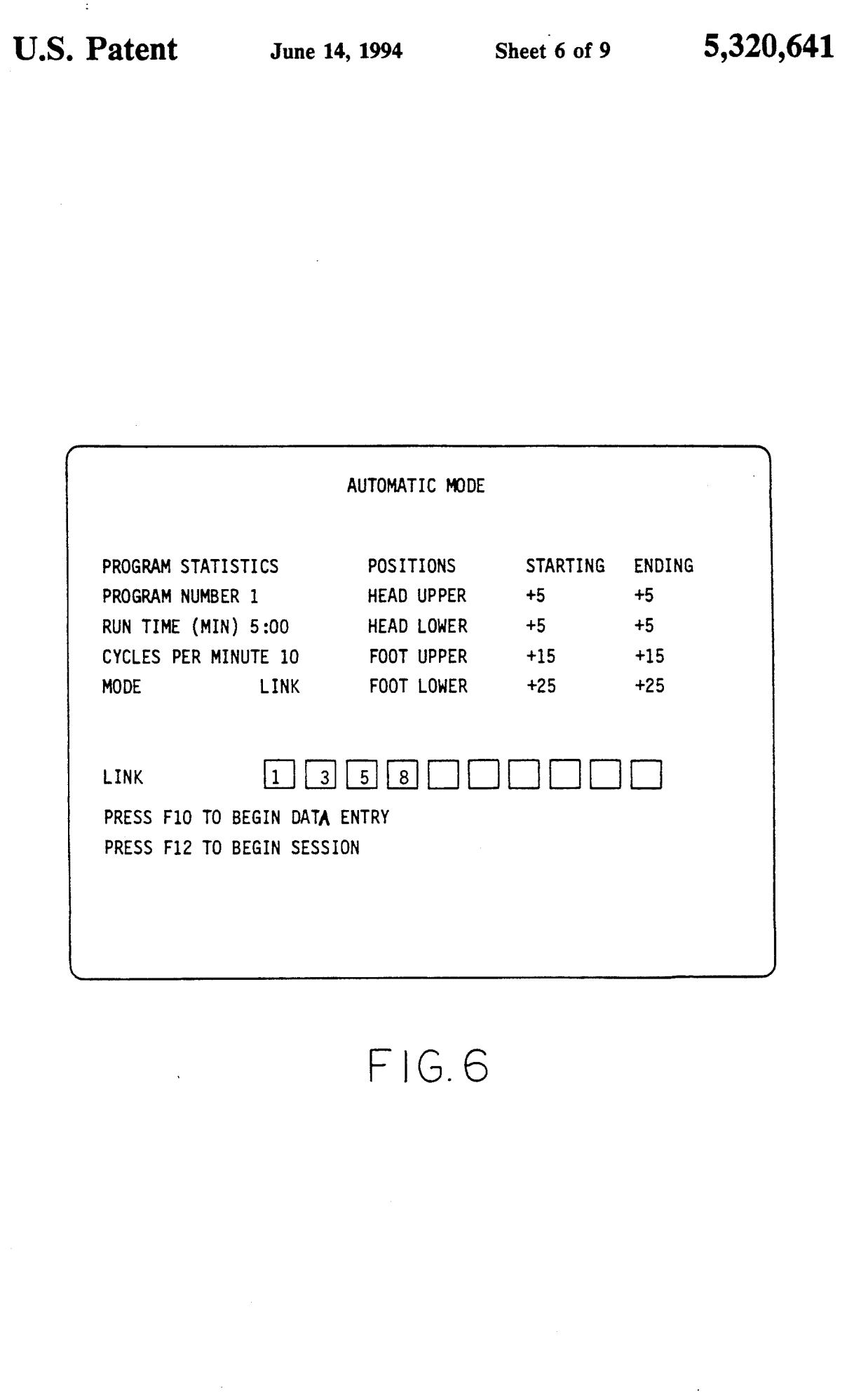

AUTOMATIC MODE

| | | | |
|---|---|---|---|
| PROGRAM STATISTICS | POSITIONS | STARTING | ENDING |
| PROGRAM NUMBER 1 | HEAD UPPER | +5 | +5 |
| RUN TIME (MIN) 5:00 | HEAD LOWER | +5 | +5 |
| CYCLES PER MINUTE 10 | FOOT UPPER | +15 | +15 |
| MODE LINK | FOOT LOWER | +25 | +25 |

LINK [1] [3] [5] [8] [ ] [ ] [ ] [ ] [ ] [ ]

PRESS F10 TO BEGIN DATA ENTRY

PRESS F12 TO BEGIN SESSION

FIG. 6

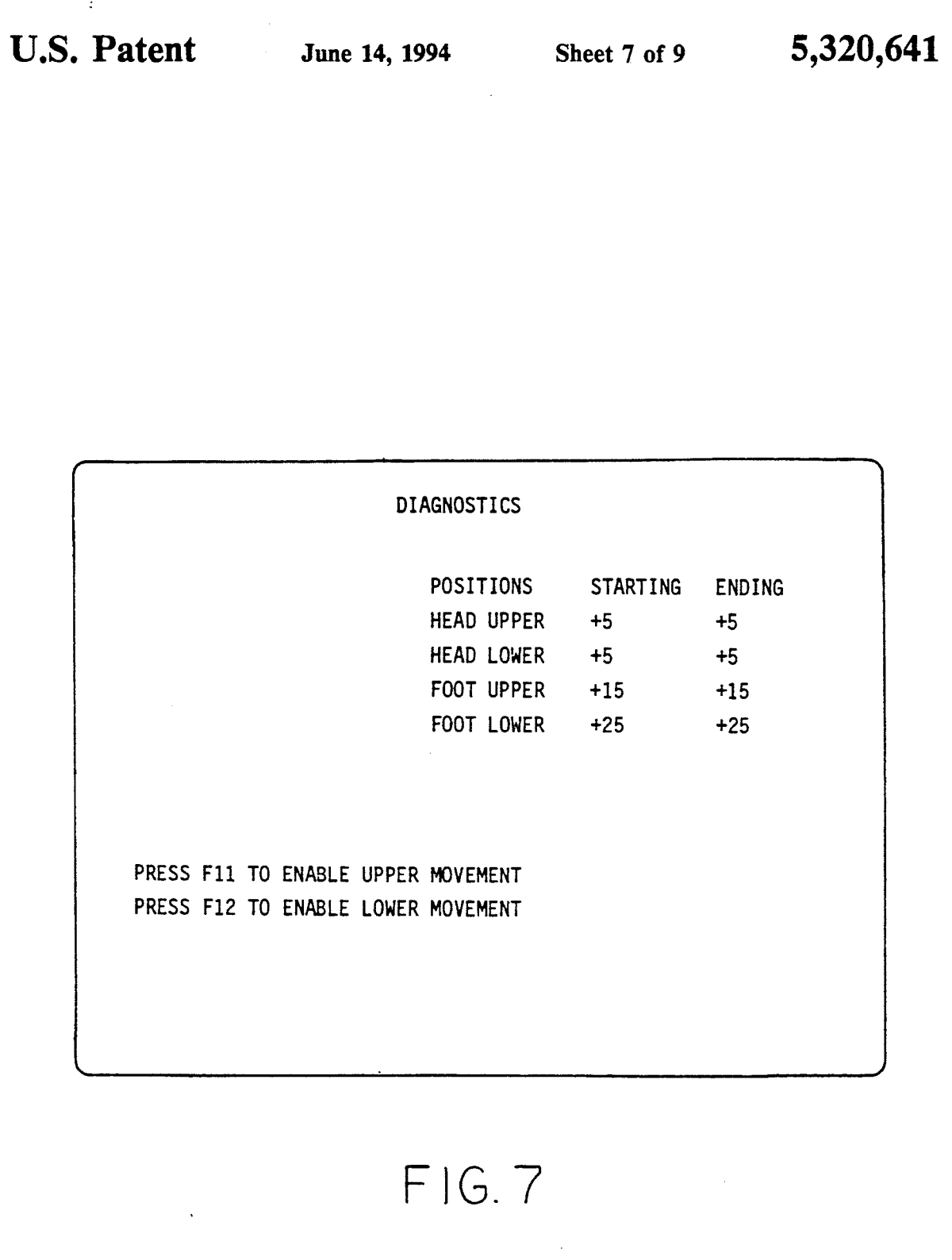

DIAGNOSTICS

| POSITIONS | STARTING | ENDING |
|---|---|---|
| HEAD UPPER | +5 | +5 |
| HEAD LOWER | +5 | +5 |
| FOOT UPPER | +15 | +15 |
| FOOT LOWER | +25 | +25 |

PRESS F11 TO ENABLE UPPER MOVEMENT
PRESS F12 TO ENABLE LOWER MOVEMENT

FIG. 7

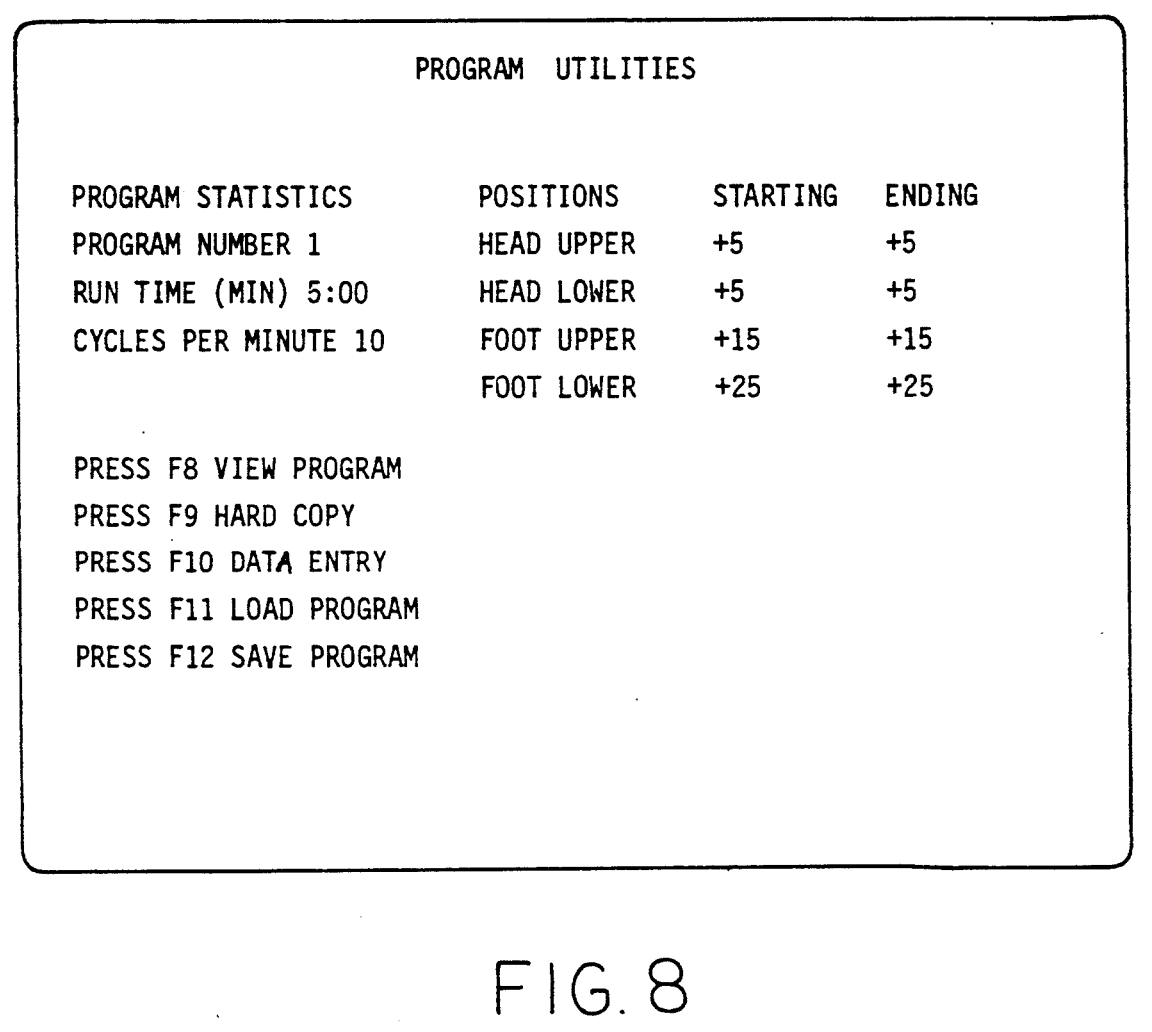

PROGRAM UTILITIES

| PROGRAM STATISTICS | POSITIONS | STARTING | ENDING |
|---|---|---|---|
| PROGRAM NUMBER 1 | HEAD UPPER | +5 | +5 |
| RUN TIME (MIN) 5:00 | HEAD LOWER | +5 | +5 |
| CYCLES PER MINUTE 10 | FOOT UPPER | +15 | +15 |
| | FOOT LOWER | +25 | +25 |

PRESS F8 VIEW PROGRAM
PRESS F9 HARD COPY
PRESS F10 DATA ENTRY
PRESS F11 LOAD PROGRAM
PRESS F12 SAVE PROGRAM

FIG. 8

COMPUTER CONTROLLED PHYSICAL THERAPY DEVICE

COMPUTER CONTROLLED PHYSICAL THERAPY DEVICE

This is a continuation-in-part of patent Ser. No. 07/843,805 filed Feb. 28, 1992 and upon patent application Ser. No. 07/902,084 filed Jun. 22, 1992 now U.S. Pat. No. 5,258,019 issued Nov. 2, 1993, both of which are based upon a parent patent application Ser. No. 07/643,945, filed on Jan. 14, 1991, which has matured into U.S. Pat. No. 5,123,916 issued Jun. 23, 1992.

TECHNICAL FIELD

The present invention relates generally to physical therapy machines, particularly those used in the field of post-trauma and post-operative spinal therapy. Specifically, the invention relates to a computer controlled physical therapy device to be used to move muscle groups in the rehabilitation of the lumbar spine and cervical spine to regain strength and function.

BACKGROUND ART

In the field of spinal therapy, it is well known that serious loss of motion, painful contractures and stiffness may occur. Further, it is also well known rehabilitation is difficult in that the normal collagen formation cannot occur and disorganized scar results which further impedes the healing process recovery.

Various devices have been developed by which spinal portion of the human body can be exercised for rehabilitative purposes. These devices have also been utilized in other, but related, exercise of the body to strengthen muscle tone, etc., even when there has been no operation. Typical of the devices developed for this field include U.S. Pat. Nos.: 2,152,431 issued to S. H. Jensen on Mar. 28, 1939; 2,598,204 issued to R. E. Allen on May 27, 1952; 3,315,666 issued to J. W. Sellnor on Apr. 25, 1967; 3,450,132 issued to C. A. Ragon, et al. on Jun. 17, 1969; 3,623,490 issued to R. F. Chisholm on Nov. 30, 1971; 3,674,017 issued to H. Stefani, Jr. on Jul. 4, 1972; 4,419,989 issued to T. E. Herbold on Dec. 13, 1983; 4,531,730 issued to R. Chenera on Jul. 30, 1985, 4,827,913 issued to A. E. Parker on May 9, 1989; 4,834,072 issued to L. M. Goodman on May 30, 1989; and 5,014,688 issued to D. Fast on May 14, 1991.

Each of these devices are designed to exercise the human body in some fashion for strengthening, stretching, relaxing, reducing weight, or some other related therapy function. None of these, however, is designed specifically for exercising a patient's spine as a rehabilitation technique following surgery or for patients suffering from post-trauma (e.g. whiplash) and chronic deconditioned spines.

There have been some devices designed specifically for therapy relative to the spine. These are described in, for example, U.S. Pat. Nos.: 1,628,369 issued to M. R. McBurney on May 10, 1927; 2,749,911 issued to L. Griffin on Jun. 12, 1956; 4,834,072 issued to L. M. Goodman on May 30, 1989; 4,953,541 issued to A. E. Parker, Jr. on Sep. 4, 1990; 5,099,828 issued to C. H. Duke on Mar. 31, 1992; and 5,123,916 issued to G. E. Riddle, et al. (the present applicants) on Jun. 23, 1992.

Other devices of the present applicants are disclosed in U.S. Patent applications Ser. Nos. 07/843,805 and 07/902,084. These two patent applications, together with the afore-cited U.S. Pat. No. 5,123,916, are incorporated herein by reference for their teachings.

The desired exercise for postoperative spinal therapy begins with the patient lying in a substantially horizontal plane. Depending upon the portion of the spine to be exercised, that portion is moved relative to portions that are fixed. For example, for cervical spine therapy, the one portion of the body remains in a fixed position while the other support portion of the device is either elevated or depressed. For example, the lower portion of the body remains fixed, while the upper portion is moved. The reverse motion can be utilized, or both portions can be moved. For lumbar spine therapy, the buttocks remain in a fixed position while the upper and lower torso portions are either elevated or depressed, or both, through movement of supports through a selected angle. These movements are usually repeated a number of times, and at a selected rate as well as the selected angle.

The devices of the prior art provide these types of movements; however, in order to change rate, angle, and/or select the portion of the body for exercise, mechanical adjustment must be made. Thus, for a given exercise of the body portion, a particular setting of the device must be made by hand. During the exercise, if any change is to be made, the device is stopped and the mechanical adjustment is made prior to resuming the exercise. For a given patient, each therapy session may require a different degree of exercise and therefore there is a special setup for each.

Accordingly, it is an object of the present invention to provide a device for spinal physical therapy wherein the degree of exercise of a patient can be modified during therapy without physical adjustment of the device by a clinician.

Another object of the present invention is to provide a spinal therapy device wherein a memory unit provides information as to the particular exercise to be given during a given therapy session.

A further object of the present invention is to provide a spinal therapy device wherein a memory unit is provided wherein a patient has input as to the extent of motion that can be tolerated such that a program of operation of the device is created to carry out a therapy session directed toward that input.

It is still another object of the present invention to provide a spinal therapy device that is controlled by a central processing unit such that input of a clinician, a patient or a pre-set array of operating parameters govern movement of body support portions to achieve a desired exercise pattern for therapy of the patient.

These and other objects and advantages of the present invention will become apparent upon a consideration of the drawings referred to hereinafter, and to a complete discussion thereof.

DISCLOSURE OF THE INVENTION

In accordance with the present invention, there is provided an improved spinal therapy device. The device has support portions for the body of a patient, with at least one support portion being moveable to exercise a selected portion of the patient's body. Motion of that at least one support portion is achieved through use of a actuator that receives operating signals from a central information processing unit. Typically, the actuator is driven by an electrical motor; however, hydraulic, pneumatic and like drives can be used. Selected operating parameters of the movement are entered into the central processing unit from memory units. These memory units include at least a memory unit accessible by the patient and a memory unit accessible by the clinician. Further, there may be a memory unit of a "standard" exercise that can input to the central processing unit to cause the body support portion to elevate, depress or otherwise move such that the patient's spinal portions are given therapeutic exercise. Where there are two moveable support portions, they can be operated separately or jointly in-phase or out-of-phase.

BRIEF DESCRIPTION OF THE DRAWINGS

FIG. 6 is a drawing illustrating a typical display of the monitor for an "automatic" mode of operation as selected from the menu of FIG. 5.

FIG. 7 is a drawing illustrating a typical display of the monitor of the present invention for "diagnostics" mode of operation as selected from the menu of FIG. 5.

FIG. 8 is a drawing illustrating a typical display of the monitor of the present invention for "utilities" mode of operation as selected from the menu of FIG. 5.

BEST MODE FOR CARRYING OUT THE INVENTION

Figure 1:
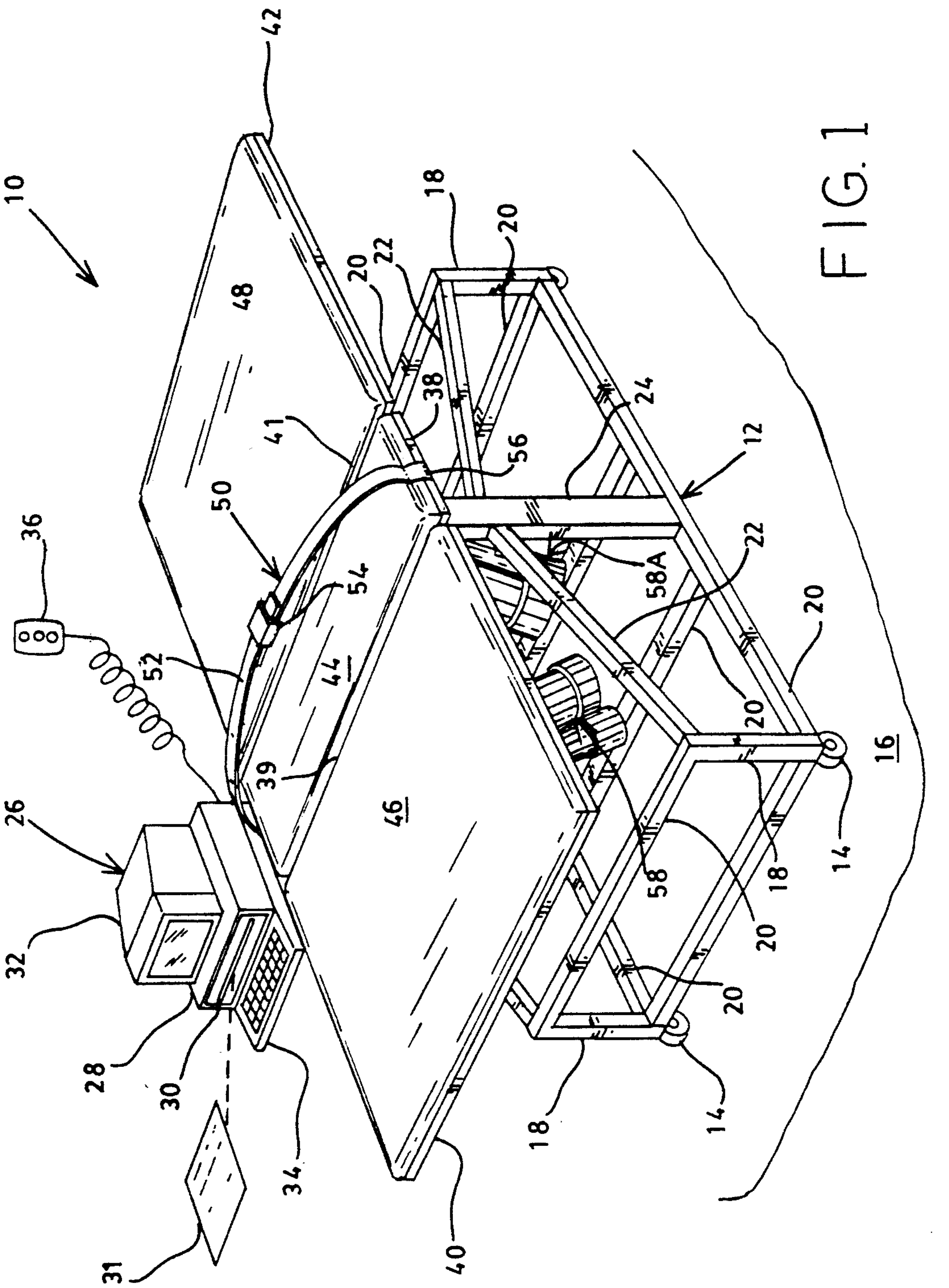
FIG. 1 is a perspective view of a lumbar spine therapy device constructed in accordance with the present invention.
Figure 2:
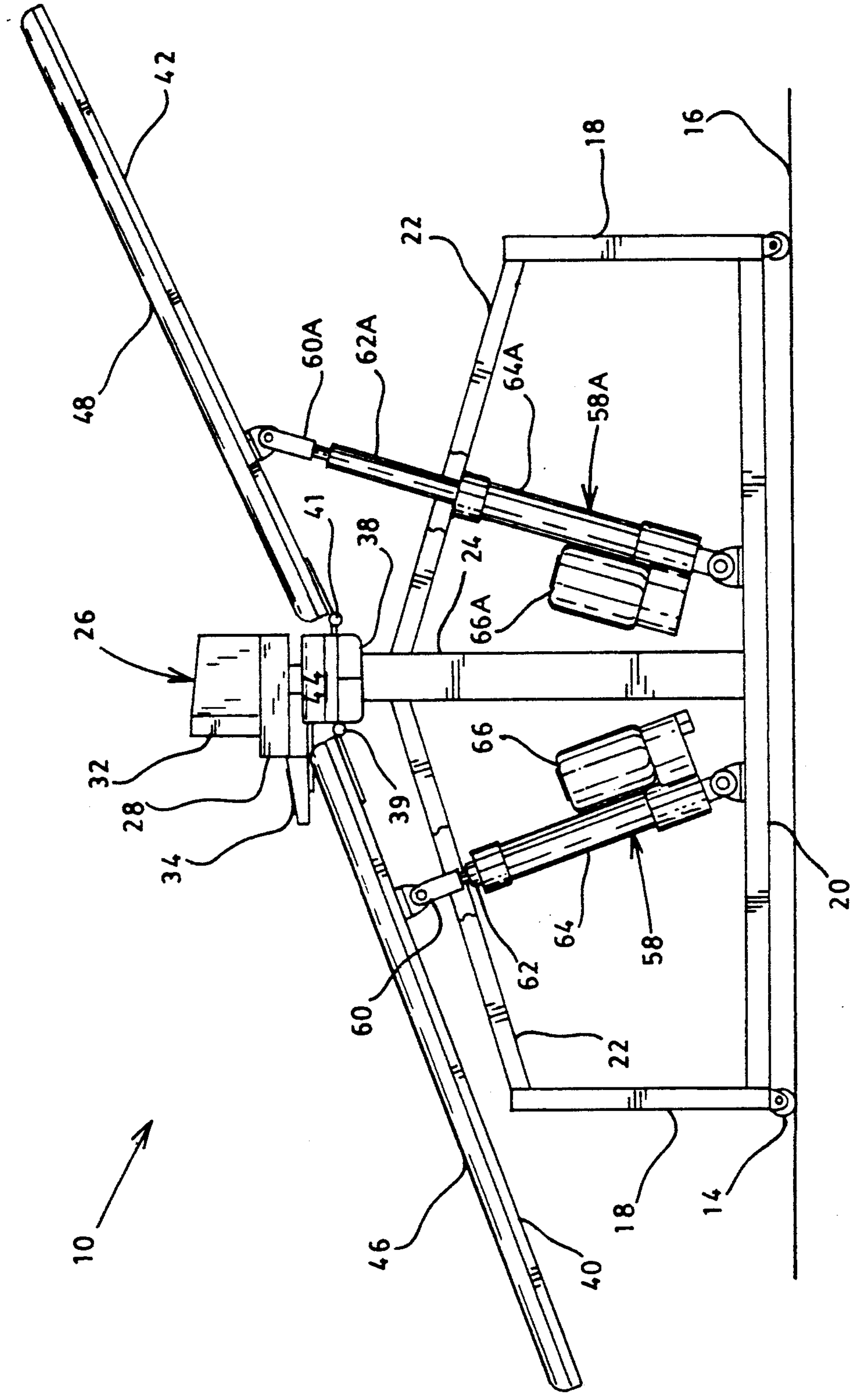
FIG. 2 is a side elevational view, partially cut away, of the device of FIG. 1.

The present invention, in one embodiment, is illustrated generally at 10 in FIGS. 1 and 2. This embodiment is of particular application for lumbar spine therapy. There is a frame member 12 which, in this embodiment, includes caster members 14 for support upon a building floor 16. The caster members permit movement of the device from place to place within a building. It will be recognized, however, the frame member 12 Can be provided with feet (not shown) to rest directly on the floor 16. The frame member 12 typically is formed from a plurality of vertical leg members 18 that are interconnected with a plurality of horizontal members 20. Further, there typically are angular brace members 22. The leg members 18, the horizontal members 22 and the angular brace members 22 typically are fabricated from either tubular or angle stock. Also, the frame member 12 typically includes vertical brace members 24 (only one shown) generally centrally located on opposite long sides of the frame member 12.

Supported from one of the vertical brace members 24 is a "command center" 26. Typically, this includes a CPU 28 with at least one floppy disk drive 30 to receive a memory disk 31, a monitor 32 and a keyboard 34. It will be understood that the CPU 28 can be located at any position within the facility, with appropriate signal communication with the keyboard 34 and monitor 32 at the device itself. The CPU 28 with the disk drive 30, the monitor 32 and the keyboard 34 can be any commercial units, and would be known to a person skilled in the art of computers. In addition, there is a patient operable input unit 36 containing various control switches therein. The patient can, for example, stop motion if pain is excessive using this input unit 36.

Mounted upon the frame member 12 are various body support members. For example, there is a substantially centrally-located body support member 38 for the support of the buttocks of a patient, this portion 38 is in a fixed position on the frame member 12. Hingedly attached to the frame along one long edge of the fixed support member 38, as at 39, is a upper torso support member 40, and a lower body support member 42 is hingedly attached to an opposite side edge of the fixed member 38, as at 41. The fixed body support 38, and the supports 40, 42 for the torso and lower body of the patient are typically provided with pads 44, 46 and 48, respectively. Typically, a patient restraint 50 is provided proximate a center of the device. This restraint typically is a belt member 52 with a clasp 54 to adjust fit to the patient. Opposite ends of the belt member 52 are fixed to the fixed support member 38 as at 56.

Elevation and depression of the torso support member 40 relative to a horizontal orientation is effected by an actuator 58. This is most clearly shown in FIG. 2. One end 60 of an extendable shaft 62 is pivotally attached to a lower surface of the torso support member 40. This shaft 62 is a portion of an "electrical pump" 64, typically Series D manufactured by Industrial Devices, Inc. of Navajo, Calif. It will be understood, however, that other servo-controlled systems which receive input signals from the CPU 28 can be substituted therefore. These would include pneumatic and hydraulic systems. The opposite end of the actuator 58 is pivotally attached to a horizontal brace member 20 of the frame member 12. The motion of the shaft 62 is effected by a motor unit 66 that receives signals from the aforementioned CPU 28 via an actuator control card 86 (see FIG. 4). Provided on the interior of the electrical pump 64 is a potentiometer (not shown) to derive a position signal of the extension of the shaft 62 for feedback to the CPU 28. Thus, as information from a selected memory (either internal or inserted via a disk 31) that directs the CPU 28, the shaft 62 is moved axially to effect a pivoting of the support member 40 at the point 39.

In the embodiment illustrated in FIGS. 1 and 2, a second actuator 58A is utilized to pivotally elevate or depress a lower body support portion 42 (as described in more detail in afore-cited patent application Ser. No. 07/902,084 and U.S. Pat. No. 5,123,916). This is substantially identical to actuator 58 and thus has a shaft 62A pivotally attached to an under surface of the support portion 42 that is moved axially by the unit 64A driven by the motor 66A. This reversible motor 66A (like motor 66) receives energizing signals through an actuator controller card that come from the CPU 28. The opposite end of the unit 64A is pivotally attached to a horizontal brace member 20. Thus, as the shaft 62A is moved axially, the body support 42 is pivoted at 41. It will be understood that a third actuator (not shown) can be used if the lower body support 42 is split into two leg support portions (not shown) as described in afore-cited patent application Ser. No. 07/902,084. In this construction the second and third actuators can be moved in-phase or out-of-phase to each other, or one only.

Figure 3:
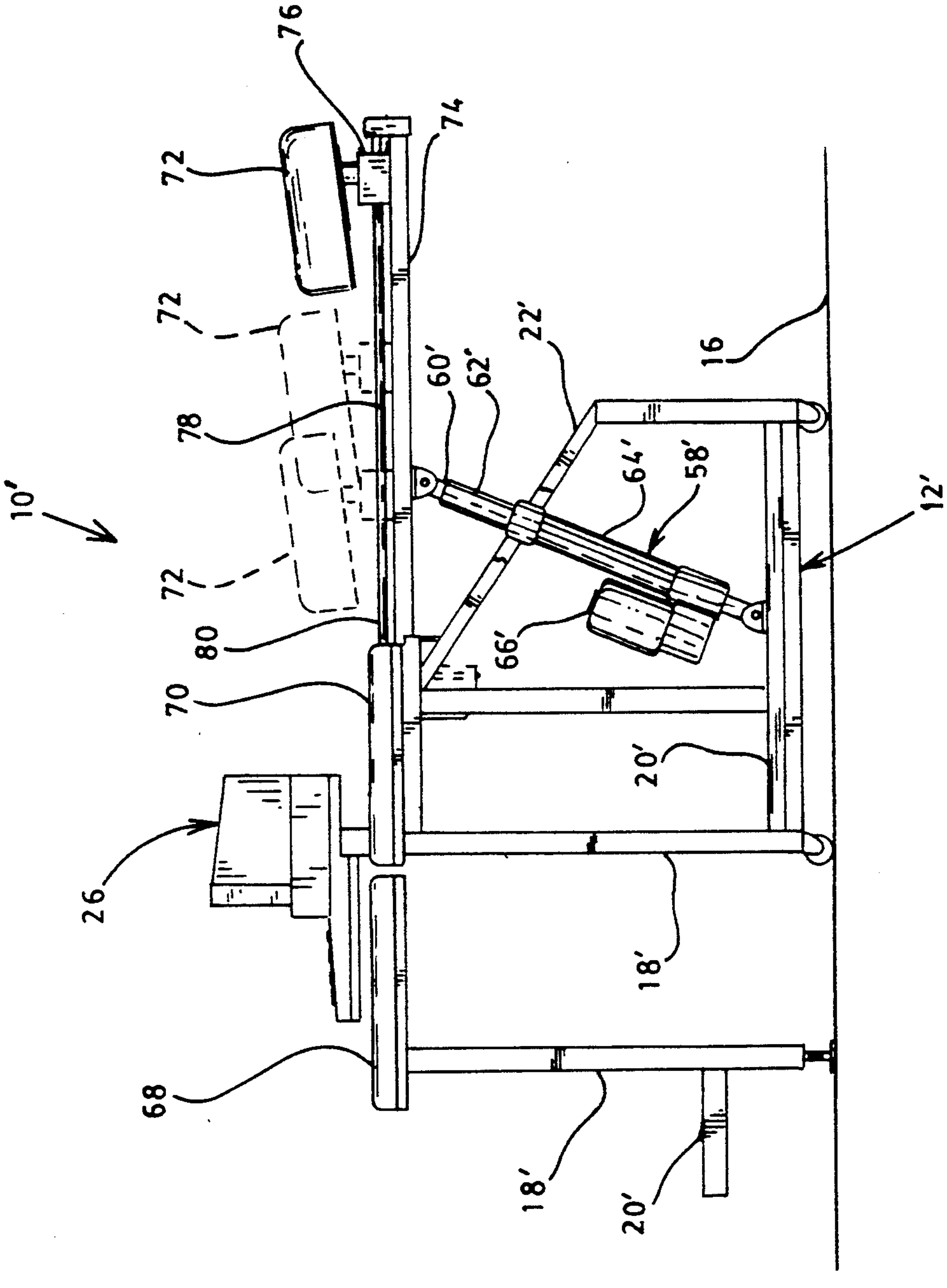
FIG. 3 is a side elevational view, partially cut away, of another embodiment of the present invention as utilized for cervical spine therapy.

Similar control for a spinal therapy device specifically for cervical spine applications is illustrated in the embodiment of FIG. 3 at 10'. The structure, except for the particular actuator, is like that shown and described in the afore-cited patent application Ser. No. 07/843,805 where details are given of the support structure including back supports 68, 70 and a head support 72 that are mounted from a frame 12'. For the purpose of this invention, it will be understood that the frame 12' is an assemblage of vertical supports 18' and horizontal members 20', together with angular braces 22'. These typically are formed from metal that is fastened in any appropriate manner, such as bolts, welding, etc. In this embodiment the head support 72 is slidably mounted on a base 76, that moves along track 78 on a support 74, such that as support 74 is either elevated or depressed while pivoting at 80, the head support 72 can move to accommodate a constant neck length of a patient. Further, the head support 72 can be initially adjusted to a starting position for a given patient. Additional positions of the head support 72 are indicated with phantom lines in FIG. 3.

The pivoting of the support 74 is effected by actuator 58'. This unit includes an axially reciprocatable shaft 62', the upper end 60' thereof being pivotally attached to an under surface of the support 74. It also includes an electrical pump unit 64' and a reversible drive motor 66', or an equivalent drive system, all of these units being the same as described relative to FIGS. 1 and 2. As above, the motor 66' is provided signals from the CPU 28 through an appropriate actuator controller card at the motor 66'.

Figure 4:
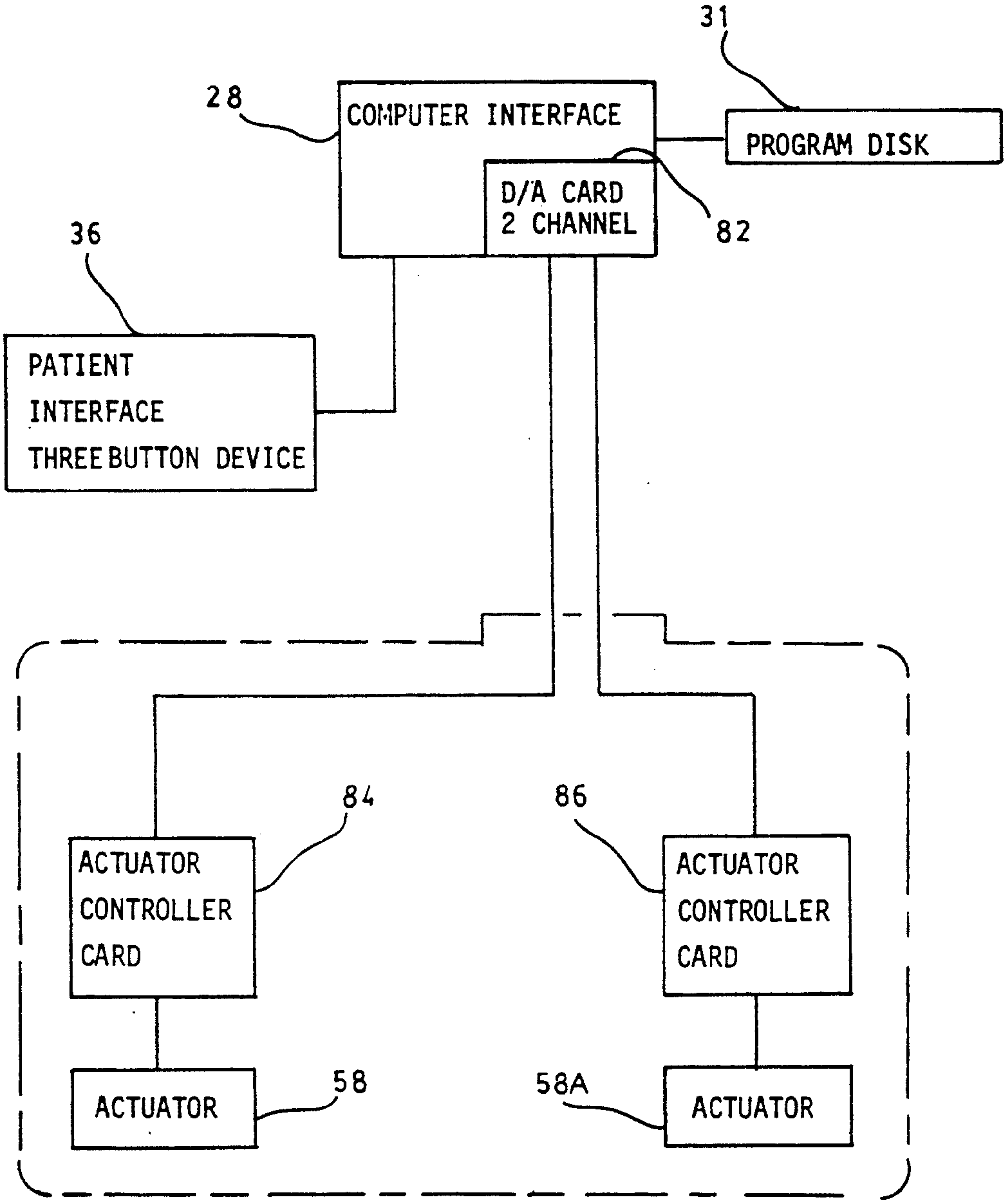
FIG. 4 is a block diagram of the elements of the computer control of the present invention.

A basic block diagram of the computer control utilized in the present invention is shown in FIG. 4. Stored within the CPU 28, in any suitable memory units 82, are the overall directions and basic software program utilized for spinal therapy. As indicated, the CPU 26 also receives data from program disks 31 and the patient interface device 36. Based upon internally and externally supplied data, the CPU 28 transmits operating signals to actuator controller cards 84, 86 that interface the two actuators 58, 58A, respectively. Position signals are returned to the CPU 28 via these cards. Of course, it will be understood that the embodiment of FIG. 3 for cervical spine therapy that there will be a single controller card (e.g , 84) for controlling the actuator 58'.

The program disk 31 can be, for example, a floppy disk memory created during a first session by a patient. At that time basic information would be input through the keyboard 34 as to name and all essential facts for medical records. Further, data can be obtained as to the maximum movements that the patient can tolerate during movement of the various body support portions (e.g., 40, 42 of FIGS. 1 and 2. This tolerance information can be used as beginning data for some future therapy sessions. The program disk 31 also can be instructions for machine operation as directed by a professional supervising the therapy. For example, specific ranges of motions can be preset for each of several therapy sessions such that when the patient information is retrieved from a memory unit, the machine will automatically function to provide the selected therapy. Although it is the principle intent of the present invention to provide control through data stored within memory units for the computer, there can be provided direct control from the keyboard 34 if desired for a particular therapy for a patient.

Figure 5:
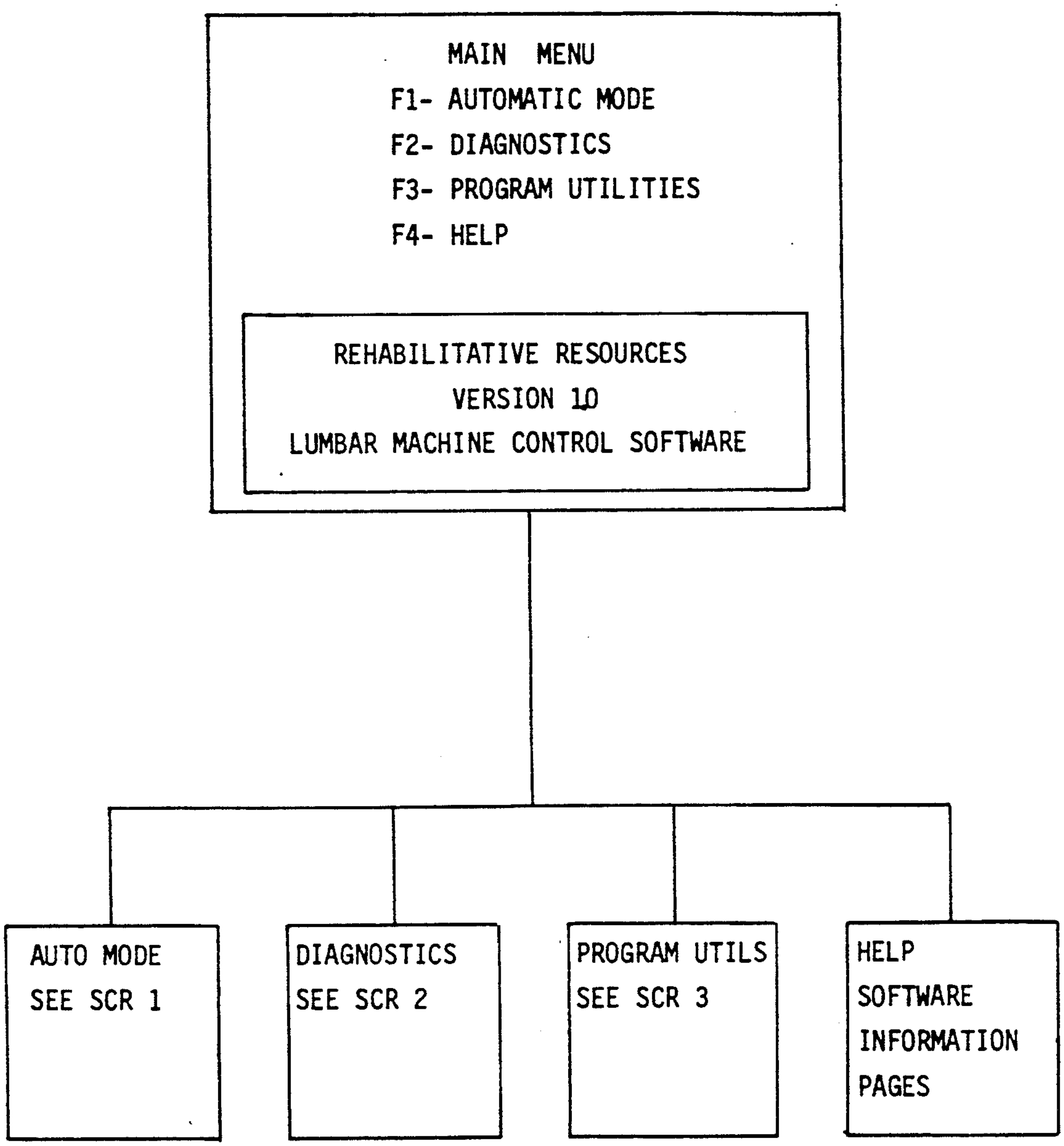
FIG. 5 is a drawing illustrating a typical display of a monitor of the present invention whereby selection of a specific applications of the device are selectable.
Figure 9:
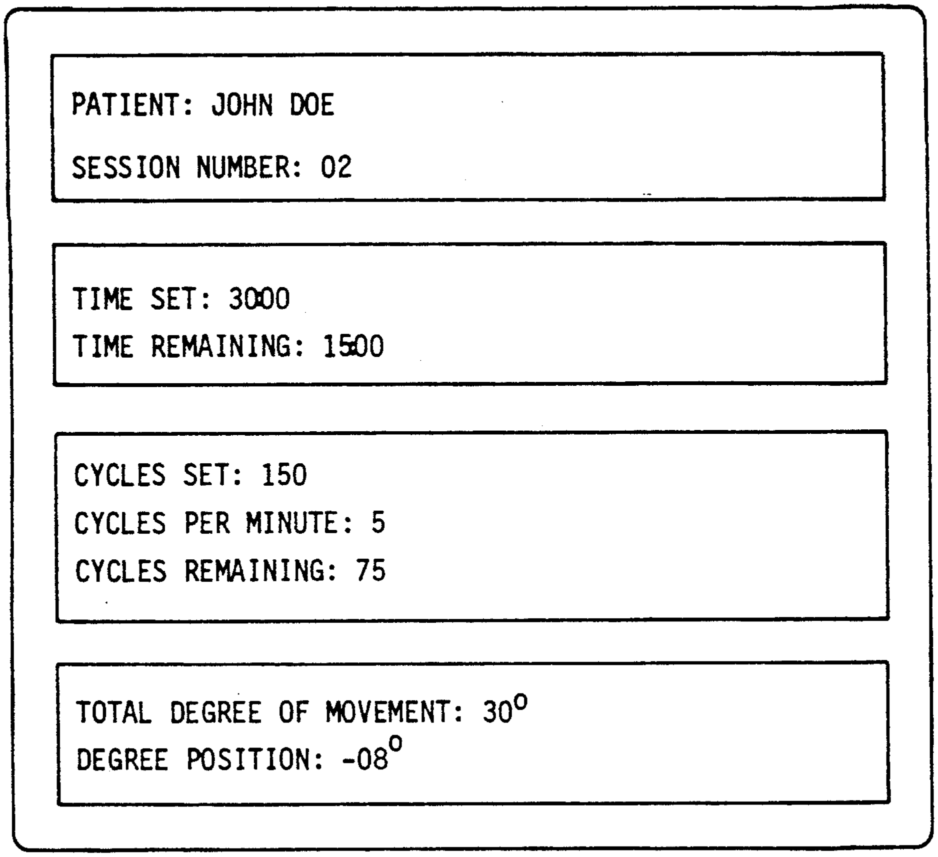
FIG. 9 is a drawing illustrating a typical display of the monitor of the present invention as occurring during a diagnostic/therapy session.

The choice of the diagnostic or automatic operation can be obtained through the internal memory 82. For example, a typical screen display on the monitor 32 is illustrated in FIG. 5. The various operating functions can be selected using the keyboard 34. Then in FIGS. 6, 7 and 8 are illustrated various screen displays that would be seen by a user if such are chosen from those shown in the screen display of FIG. 5. Although not shown, the "Help" selection would give the user further instructions as to choices, etc. A typical screen display occurring during a session is shown in FIG. 9. It will be recognized by persons skilled in the art that the particular legends on these screens can be changed depending upon the user and upon particular therapy needs.

From the foregoing it will be understood by persons skilled in the art how the body support portions of the present invention are moved from an external control. This eliminates any physical adjustment of levers, arms, etc. of the machine to change stroke length, frequency, etc. of the body support portions. Thus, any of the parameters can be easily changes throughout the therapy session, these changes even being effected by the patient if necessary or desired.

Accordingly, described herein is an improved spinal therapy device which gives great latitude to the therapy that can be effected upon a patient. While some portions of the invention are described in great detail, this is for the purpose of describing a "best mode" and not for the purpose of limitation of the invention. Rather, the invention is to be limited only by the appended claims and their equivalents.

We claim:

1. A diagnostic and therapy device for analyzing and treating post-trauma, post-operative and other disorders of a spine of a patient by moving muscle groups surrounding portions of the spine, the device comprising:

a frame for structurally supporting loads applied to said device by the patient and for transferring the loads to a building floor;

a stationary support portion mounted on said frame for receiving a buttocks portion of the patient;

a first pivoting support member for supporting a torso portion of the patient, said first pivoting support member having a first end pivotally attached to said frame proximate one side edge of said stationary support portion;

a first actuating unit having a shaft with a first end pivotally attached to said first pivoting support member, a cylinder having a first end at least partially enclosing a second end of said shaft, said cylinder having a second end pivotally attached to said frame, said shaft axially moveable within said cylinder by action of a reversible motor, said first actuating unit providing for axial extension and contraction to achieve pivotal oscillation of said first pivoting support member about said first end through a selected angle from a horizontal plane, said first actuating unit providing an electrical signal corresponding to said axial extension and contraction;

a second pivoting support member for supporting a lower body portion of the patient, said second pivoting support member having a first end pivotally attached to said frame proximate a second side edge of said stationary support portion;

a second actuating unit having a shaft with a first end pivotally attached to said second pivoting support member, a cylinder having a first end at least partially enclosing a second end of said shaft, said cylinder having a second end pivotally attached to said frame, said shaft axially moveable within said cylinder by action of a reversible motor, said second actuating unit providing for axial extension and contraction to achieve pivotal oscillation of said second pivoting support member about said first end through a selected angle from the horizontal plane, said second actuating unit providing an electrical signal corresponding to said axial extension and contraction;

a data central processing unit, said central processing unit receiving said electrical signals from, and providing actuating signals to, said first and second actuating units;

a first data storage memory for storing general operating instructions for said device in said central processing unit;

further data storage memory for storing health related information about the patient and instructions for patient oriented motion of said first and second pivoting support members in said central processing unit; and circuit elements connecting said central processing unit with said first and second actuating units to effect the pivoting of said first and second pivoting support members through said selected angles according to data within said first and further data storage memories.

2. The device of claim 1 wherein said first pivoting support member is provided with a headrest, and pivoting oscillation of said first pivoting support member provides for diagnostics and therapy of cervical muscle groups associated with the spine of the patient, said headrest mounted on said first pivoting support member on a slide member whereby said headrest moves along said slide member as said first pivoting support member is pivoted through said selected angle with respect to the horizontal plane.

3. The device of claim 1 wherein said central processing unit is provided with a data input keyboard for introducing data into said data storage memory unit and said further data storage memory unit, and with a monitor to display selected data from said data storage memory unit and said further data storage memory unit, and data from said keyboard.

4. The device of claim 3 wherein said data input keyboard and said monitor are mounted from said frame.

5. The device of claim 4 wherein said central processing unit is mounted from said frame.

6. The device of claim 1 further comprising a portable control unit connected to said central processing unit, said portable control unit for operation by the patient supported on said device.

7. A diagnostics and therapy device for analyzing and treating post-trauma, post-operative and other disorders of a spine of patient by moving muscle groups surrounding portions of the spine, the device comprising:

a frame for structurally supporting loads applied to said device by the patient and for transferring the loads to a building floor;

a stationary support portion mounted on said frame for receiving a buttocks portion of the patient;

a first pivoting support member for supporting a torso body portion of the patient, said first pivoting support member having a first end pivotally attached to said frame proximate one side edge of said stationary support portion;

a first actuating unit having a shaft with a first end pivotally attached to said first pivoting support member, a cylinder having a first end at least partially enclosing a second end of said shaft, said cylinder having a second end pivotally attached to said frame, said shaft axially moveable within said cylinder by action of a reversible motor, said first actuating unit providing for axial extension and contraction to achieve pivotal oscillation of said first pivoting support member about said first end through a selected angle from a horizontal plane, said first actuating unit providing a feedback signal related to axial movement of said shaft of said first actuating unit;

a second pivoting support member having a first end pivotally attached to said frame proximate a second side edge of said stationary support portion, said second side edge being oppositely disposed from said one side edge, said second pivoting support member for supporting a lower body portion of the patient;

a second actuating unit having a shaft with a first end pivotally attached to said second pivoting support member, a cylinder having a first end at least partially enclosing a second end of said shaft, said cylinder having a second end pivotally attached to said frame, said shaft axially moveable within said cylinder by action of a reversible motor, said second actuating unit providing for axial extension and contraction to achieve pivotal oscillation of said second pivoting support member about said first end through a further selected angle from the horizontal plane, said second actuating unit providing a feedback signal related to axial movement of said shaft of said second actuating unit;

a headrest mounted on a slide member attached to said first pivoting support member for supporting a head of the patient whereby said headrest moves along said slide member as said first pivoting support member is pivoted through said selected angle so as to provide diagnostics and therapy of cervical muscle groups;

a data central processing unit attached to said frame for receiving said feedback signals from said first and second actuating units, and for sending actuating signals to said motors of said first and second actuating units;

a first data storage memory for storing general operating instructions for said device in said central processing unit;

further data storage memory for storing health related information about the patient and instructions for patient oriented motion of said first and second pivoting support members in said central processing unit;

a data input keyboard attached to said frame, said data input keyboard providing for placing data into said first and further data memory units;

a monitor attached to said frame proximate said keyboard to display information stored in said first and further data memory units and information data being provided by said keyboard;

a portable control unit connected to said central processing unit, said portable control unit for operation by the patient supported on said device; and circuit elements connected said central processing unit with said first and second actuating units to effect said pivotal oscillations of said first and second pivoting support members through said selected angle and said further selected angle, respectively, to provide said selected exercising of said muscle groups according to data within said first and further data storage memories and said feedback signals from said first and second actuating units.

8. A diagnostics and therapy device for analyzing and treating post-trauma, post-operative and other disorders of a spine of a patient by moving muscle groups surrounding portions of the spine, said device comprising:

a frame for structurally supporting loads applied to said device by the patient and for transferring the loads to a building floor;

a stationary support portion, having a support surface, mounted on said frame, said support surface of said stationary support portion for receiving a portion of the patient;

a first pivoting support member, having a support surface and a first end, said first end pivotally attached to said frame proximate one edge of said stationary support portion, said support surface of said first pivoting support member for receiving a further portion of the patient;

a first actuating unit for causing said first pivoting support member to be pivotally oscillated at a selected angle with respect to a horizontal plane, said first actuating unit providing a feedback signal related to movement of said first pivoting support member, said first actuating unit having a) a shaft having a first end pivotally attached to a lower surface of said first pivoting support member, and a second end, b) a cylinder having an open first end receiving said second end of said shaft, and a closed second end pivotally attached to said frame, and c) a reversible motor engaged with said second end of said shaft for causing said shaft to be reciprocated within said cylinder;

a data central processing unit for receiving said feedback signal from said first actuating unit and for supplying drive signals to said reversible motor;

a first data storage memory for storing general operating instructions for said device in said central processing unit;

further data storage memory for storing health-related information about the patient and instructions for patient-oriented motion of said first pivoting support member in said central processing unit;

circuit elements connecting said central processing unit with said first actuating unit to effect the pivoting of said first pivoting support member through said selected angle according to data within said first and further data storage memories; and a portable control unit connected to said central processing unit for operation by the patient supported on said device to effect data input to said central processing unit by the patient and thus effect pivoting of said first pivoting support member.

9. The device of claim 8 wherein said stationary portion supports a buttocks portion of the patient and said first pivoting support member supports a torso portion of the patient, said device further comprising:

a second pivoting support member having a first end pivotally attached to said frame proximate a second edge of said stationary support, oppositely-disposed from said first edge, for support of a lower portion of the patient;

a second actuating unit for causing said second pivoting support member to be pivotally oscillated at a further selected angle with respect to the horizontal plane, said second actuating unit providing a feedback signal related to movement of said second pivoting support member, said second actuating unit having a) a shaft having a first end pivotally attached to a lower surface of said second pivoting support member, and a second end, b) a cylinder having an open first end receiving said second end of said shaft, and a closed second end pivotally attached to said frame, and c) a reversible motor engaged with said second end of said shaft for causing said shaft to be reciprocated within said cylinder; and circuit elements connecting said central processing unit with said second actuating unit to effect the pivoting of said second pivoting support member through said further selected angle according to data within said first and further data storage memories.

10. The device of claim 8 further comprising:

a slideway mounted upon said support surface of said first pivoting support member; and a headrest slidably mounted on said slideway, said headrest for supporting a head of the patient, whereby said headrest moves along said slide member as said first pivoting support member is pivoted through said selected angle so as to provide diagnostics and therapy of cervical muscle groups of the patient.

* * * * *